(12) United States Patent
Lazzareschi et al.

(10) Patent No.: US 12,140,572 B2
(45) Date of Patent: Nov. 12, 2024

(54) REAL TIME TISSUE PAPER PRODUCTION CORRECTION DEVICE

(71) Applicant: SOFIDEL S.P.A., Porcari (IT)

(72) Inventors: Luigi Lazzareschi, Porcari (IT); Massimiliano Vannucchi, Porcari (IT); Francesco Sebastiani, Porcari (IT)

(73) Assignee: SOFIDEL S.P.A., Porcari (IT)

( * ) Notice: Subject to any disclaimer, the term of this patent is extended or adjusted under 35 U.S.C. 154(b) by 287 days.

(21) Appl. No.: 17/713,866

(22) Filed: Apr. 5, 2022

(65) Prior Publication Data
US 2022/0317003 A1 Oct. 6, 2022

(30) Foreign Application Priority Data

Apr. 6, 2021 (IT) .................... 102021000008453

(51) Int. Cl.
| | | |
|---|---|---|
| *G01N 3/08* | (2006.01) | |
| *G01G 17/02* | (2006.01) | |
| *G01N 33/34* | (2006.01) | |
| *B25J 15/00* | (2006.01) | |
| *G01B 11/08* | (2006.01) | |

(52) U.S. Cl.
CPC ............... *G01N 3/08* (2013.01); *G01G 17/02* (2013.01); *G01N 33/34* (2013.01); *B25J 15/0028* (2013.01); *G01B 11/08* (2013.01); *G01N 2203/0282* (2013.01)

(58) Field of Classification Search
None
See application file for complete search history.

(56) References Cited

U.S. PATENT DOCUMENTS

2003/0029959 A1* 2/2003 Fujiwara ............... B65H 19/28
242/528

FOREIGN PATENT DOCUMENTS

| EP | 1063190 A2 | 12/2000 | |
|---|---|---|---|
| EP | 1530044 A1 | 5/2005 | |
| EP | 1530044 B1 | 3/2011 | |
| WO | WO-2019185438 A1 * | 10/2019 | ......... B65H 19/2269 |

* cited by examiner

*Primary Examiner* — Brandi N Hopkins
*Assistant Examiner* — Nigel H Plumb
(74) *Attorney, Agent, or Firm* — McGlew and Tuttle, P.C.

(57) ABSTRACT

A device for providing improved measurements of logs. The device includes a feed path of the logs, configured to feed the logs in a direction orthogonal to the axis of the logs; and one or more pick-up members spaced from one another in a direction transverse to the feed path of the logs. The pick-up members are adapted to pick up individual logs from a pick-up position along the feed path; and transfer each log from the measuring position back to the feed path substantially in the position in which it was picked up.

27 Claims, 22 Drawing Sheets

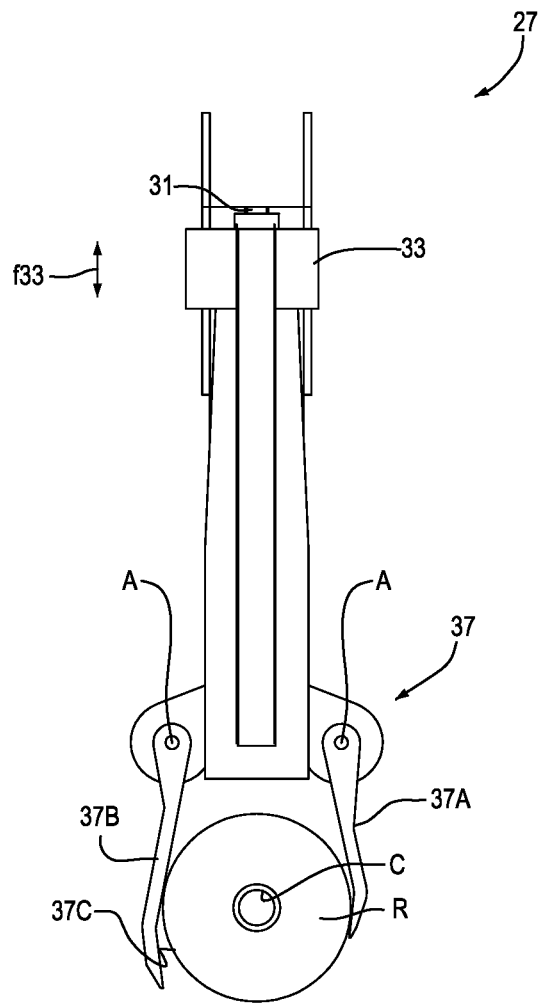
Fig.8D

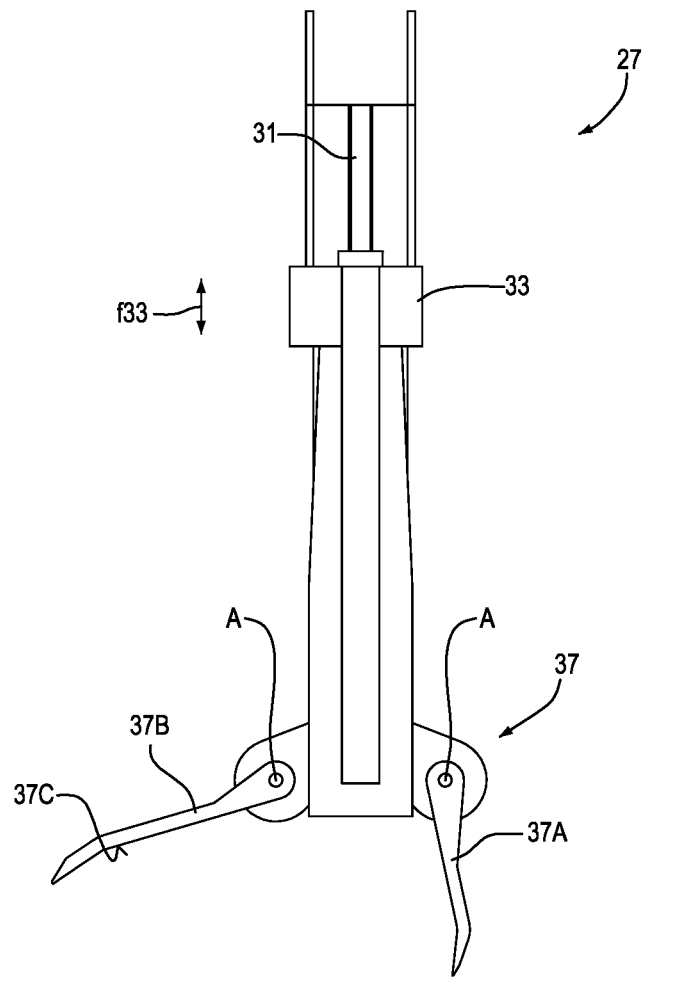
Fig.8H

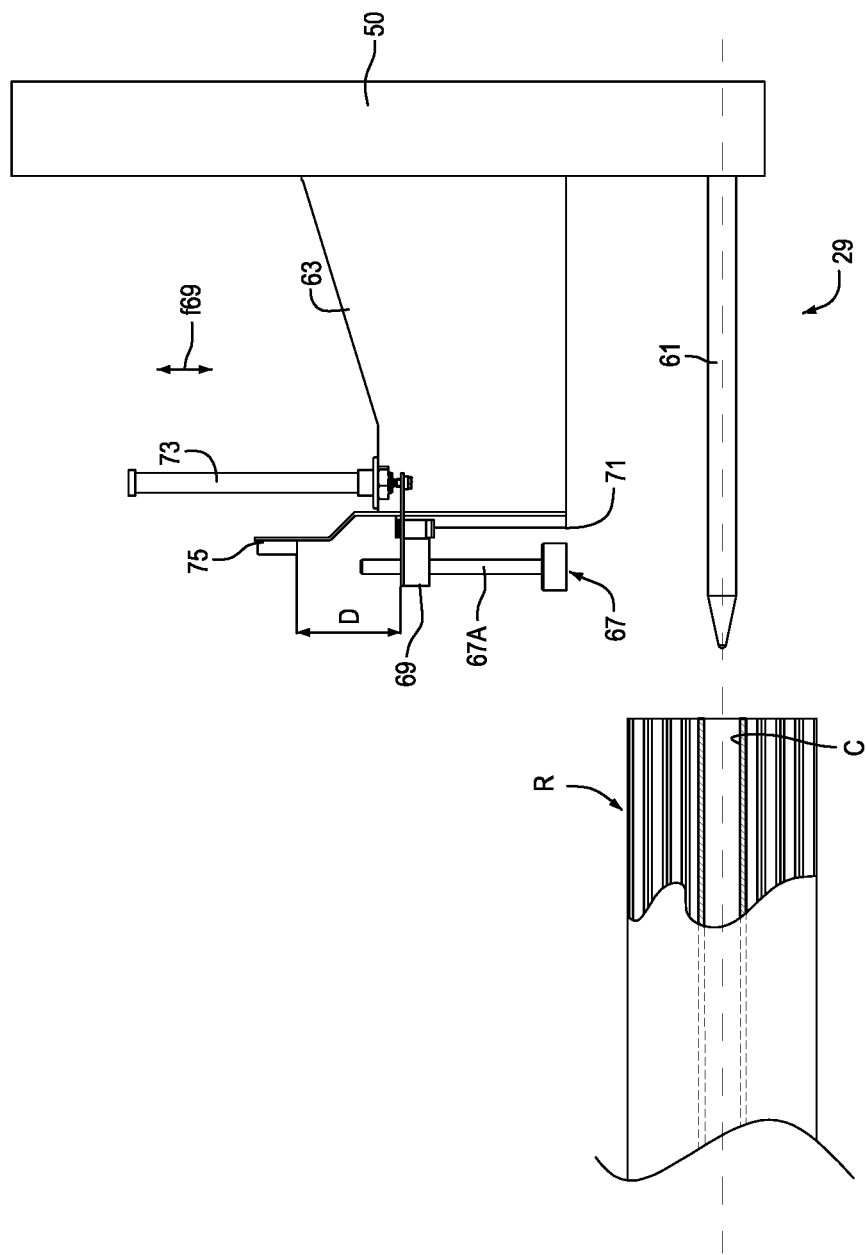

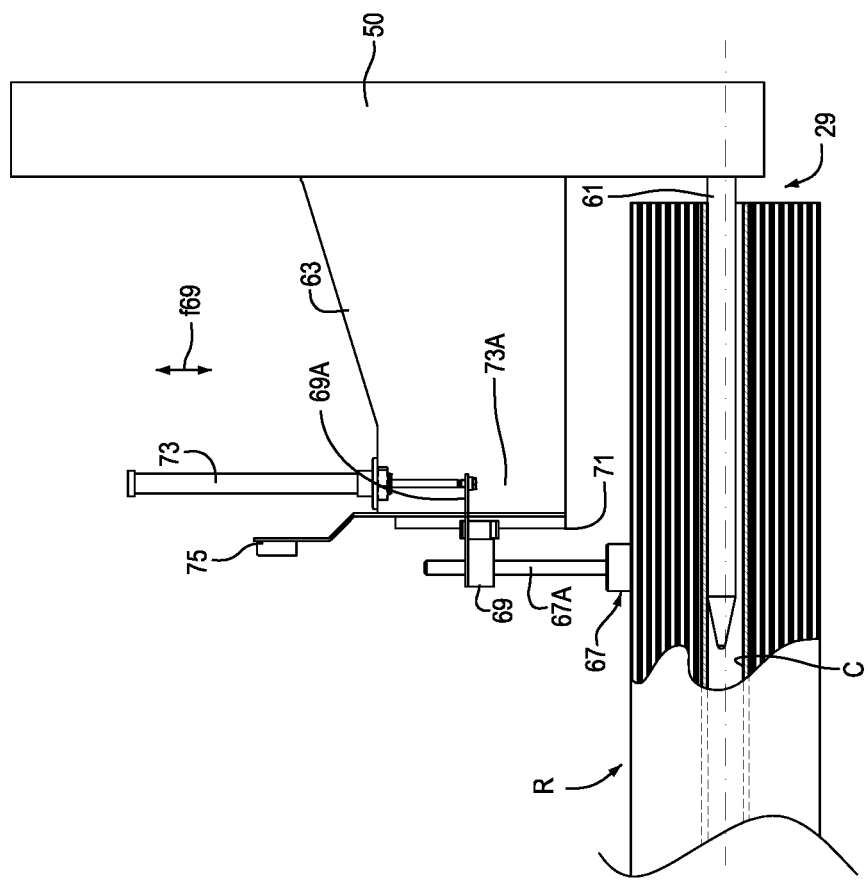

REAL TIME TISSUE PAPER PRODUCTION CORRECTION DEVICE

TECHNICAL FIELD

The present invention relates to improvements to devices and methods for measuring one or more characteristic, i.e., parameters or sizes of a log of web material, for example but not exclusively logs of tissue paper, useful for controlling the production process.

BACKGROUND ART

In many industrial fields in which logs of wound web material are produced, it is necessary to measure one or more parameters, i.e., physical features of the logs, in order to take action on production parameters to maintain the physical characteristics, i.e., the parameters of the logs produced within a predetermined range.

Typically, among the parameters, i.e., the physical characteristics of the logs, weight is important in the field of tissue paper, used to produce rolls of toilet tissue, kitchen towels and similar articles. A further parameter, i.e., characteristic, which in some cases is useful for controlling the production process is firmness. The diameter of the logs can also be important for controlling production.

Typically, the measurements of at least some of these parameters takes place in a laboratory, on samples of logs picked up from the production line. This measuring method is not satisfactory, as the measurement obtained outside the line does not allow real time correction of the production parameters in order to correct any divergences of the firmness measured relative to the values desired.

A device and a method to overcome this drawback are disclosed in EP1530044. In the measuring system disclosed therein each log produced is fed along a feed path with a movement parallel to the axis of the log. Located along the feed path is a device for firmness measuring, provided with a wheel positioned at a distance with respect to a surface on which the log is supported, so as to apply a known compressive force to the log, when the log passes between the wheel and the supporting surface. The thrust exerted by the log on the wheel causes lifting of the wheel. The displacement of the wheel is a function of the diameter of the log and of the compressive deformation (compression) of the log caused by the force applied by the wheel.

This system is particularly complex and requires the logs to be fed in the direction of their axis. This condition is incompatible with the configuration of the majority of production lines for logs of tissue paper, where the logs produced by a rewinder are fed along the feed path by rolling and hence orthogonally to their axis.

Moreover, the measuring system disclosed in EP1530044 is not particularly precise. In fact, due to the configuration of the measuring system, any compression deformations of the tubular winding core on which the log is formed are erroneously added to the compression of the wound material. The more deformable the tubular winding core, the greater this measurement defect will be. In an effort to reduce consumables, increasingly thin winding cores are produced, making them increasingly deformable by compression and tending to make the firmness measurement imprecise.

To solve some of the defects of the device described in EP1530044, more reliable systems for measuring the firmness of the logs have been developed and are disclosed in WO2019185438. The systems and the methods disclosed herein are much more efficient and precise than those of the prior art and overcome many of the intrinsic limits. Nonetheless, there is still room for further improvements, in particular in order to obtain more precise measurements and simpler measurement devices.

SUMMARY OF THE INVENTION

According to an aspect, disclosed herein is a device for measuring parameters of a log of wound web material, including a feed path for the logs, configured to feed the logs in a direction orthogonal to the axis of the logs, and one or more pick-up members, for example two pick-up members spaced from one another in a direction transverse to the feed path of the logs. The pick-up member or members is/are adapted to pick up individual logs from a pick-up position along the feed path and to transfer each log from the measuring position back to the feed path.

The number of pick-up members can depend on the length of the logs to be handled. For short logs, i.e., with a limited longitudinal dimension, a single pick-up member may suffice. For longer logs, a pair of pick-up members may be required, or even more than two pick-up members aligned with one another in a direction transverse to the direction of movement of the logs along the feed path.

The device can be controlled to randomly pick up logs, and to measure one or more parameters of these logs. In some embodiments, the device can be configured to measure only the weight of the log. In other embodiments the device can be configured to measure only the firmness of the log.

In particularly advantageous embodiments, the device can be configured to measure both the firmness and the weight of the log.

To obtain further useful information, the device can also measure the diameter of the log, or can be combined with a different device that measures the diameter of the log, even in a position distanced from the point in which the device is located.

In embodiments described herein, the device has many advantages with respect to known devices, including its simplicity and limited footprint, while maintaining high measurement precision and flexibility.

The device thus configured can be inserted in existing converting lines, i.e., lines for producing logs from reels of large diameter, for instance, substantially without requiring to modify the layout thereof, or with minor modifications. This is facilitated by the small footprint of the device, which can be inserted into existing spaces along a previously installed line.

In advantageous embodiments, the pick-up member(s) is(are) adapted to measure at least one parameter of the picked-up log, while the log is engaged with the pick-up member(s). In particular, each pick-up member can comprise a respective weight sensor, for example a load cell, which allows the weight of the log picked up by the pick-up members to be measured, while the log is still engaged with said pick-up member(s). This allows fast measurements to be obtained with a very compact structure of the device.

Advantageously, the pick-up member(s) is(are) adapted to transfer each log picked up from the measuring position back to the pick-up position along the feed path of the logs. In other terms, the logs are picked up from the feed path in one point and re-inserted into the feed path in the same point in which they were picked up. This contributes to the simplicity and compactness of the device.

In advantageous embodiments, each pick-up member comprises a gripper with a first jaw and a second jaw, the first jaw being located upstream of the second jaw with respect to the direction of feed of the logs along the feed path. In embodiments disclosed herein, the first jaw and the second jaw pivot about respective pivot axes orthogonal to the direction of feed of the logs along the feed path and parallel to the axes of the logs and their movement can advantageously be controlled by a first actuator for controlling the movement of the first jaw and by a second actuator for controlling the movement of the second jaw. The first and the second actuator can be independent and controlled in a manner coordinated with respect to each other, to perform suitable maneuvers with the jaws of the grippers.

As will be described below, with reference to an exemplary embodiment, this allows operations to pick up and release the individual logs in the flow of the logs along the feed path, without interfering with or obstructing the normal feed of the logs.

Feed of the logs along the path can take place by rolling under the effect of gravity, the path being defined by an inclined chute, for instance.

In particularly simple embodiments, the device can comprise only one or more pick-up members, with which sensors, for example load cells for measuring weight, are associated.

However, in more complex and complete embodiments, the measuring device can have a measuring system of the log firmness. This system can comprise a pair of blocking heads, adapted to block a log by means of tailstocks, located above the feed path and at the sides of the feed path. At least one of the blocking heads, and preferably each blocking head, comprises a log firmness measuring member. In embodiments, the blocking heads are aligned transverse to the feed path along a direction orthogonal to the direction of feed of the logs along the feed path and parallel to the direction of the axes of the logs along the feed path. The pick-up member(s) is(are) adapted to position each picked-up log in a measuring position, in which the log interacts with the blocking heads and with the log firmness measuring member, associated with the blocking head.

Each log firmness measuring member can, for example, comprise a presser adapted to apply a predetermined load against the surface of a log picked up from the feed path and a measuring arrangement of the degree of penetration of the presser in the log as a result of a predetermined load applied by the presser.

Further advantageous features and embodiments of the device are defined in the appended claims, which form an integral part of the present description.

According to a further aspect, described herein is a method for manufacturing logs of web material, comprising the following steps:
  sequentially producing logs of web material;
  feeding the logs of web material in a feed path, in which the logs of web material are fed in a direction orthogonal to the axis of the logs;
  by means of one or more pick-up members spaced from one another in a direction transverse to the feed path of the logs, picking up a log from a pick-up position along a feed path of the logs;
  measuring at least one parameter of the picked-up log;
  returning, by means of the pick-up member(s), the log in the feed path.

Further advantageous embodiments of the method are described below and defined in the appended claims.

BRIEF DESCRIPTION OF THE DRAWINGS

The invention will be better understood by following the description and the accompanying drawings, which illustrate a non-limiting exemplary embodiment of the invention. More in particular, in the drawings:

FIGS. 8A to 8J show a sequence of picking up a log from the feed path and repositioning the log in the feed path after measurement;

FIGS. 9A-9E show a sequence of measuring the log firmness.

DETAILED DESCRIPTION

Figure 1:
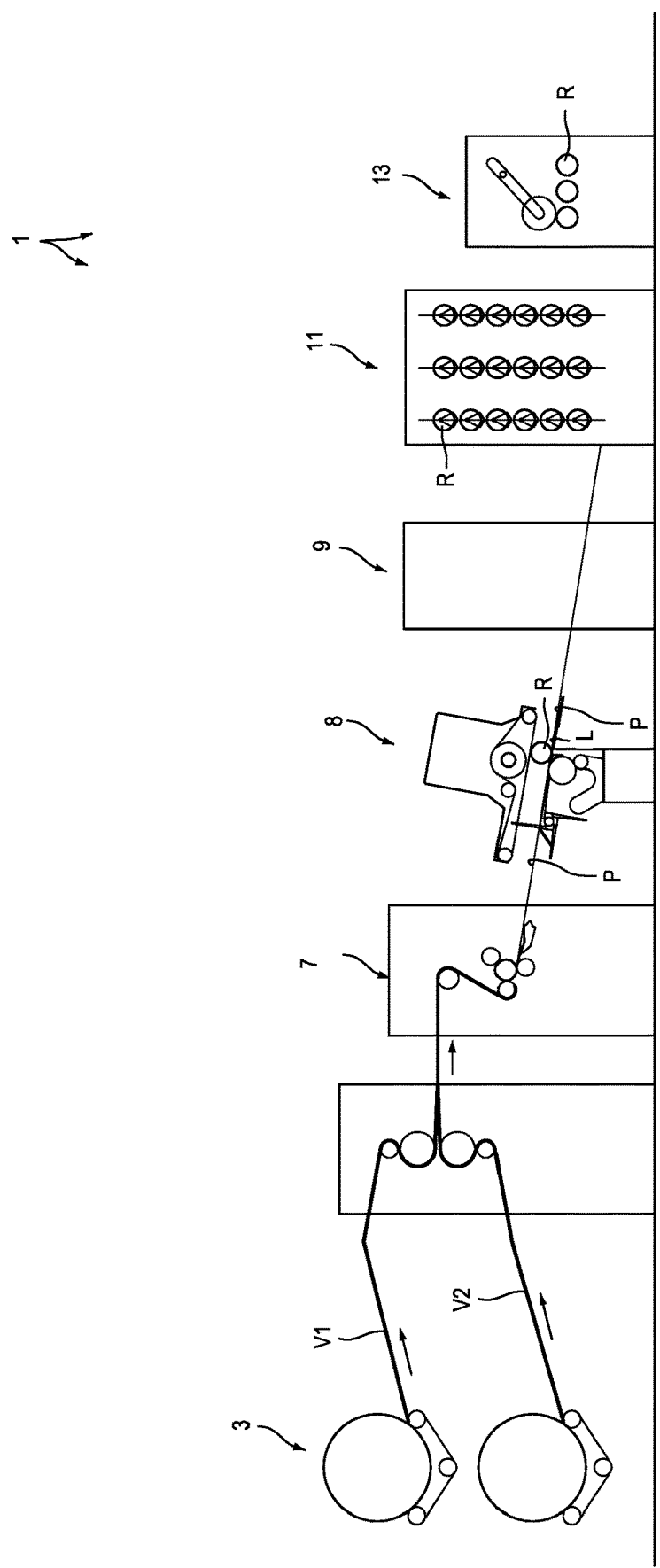
FIG. 1 shows a schematic side view of a portion of a production line of logs of tissue paper.

FIG. 1 schematically shows a side view of a portion of a converting line 1 for producing logs R of tissue paper. The converting line 1 comprises a rewinder 7, that winds one or more plies of tissue paper V1, V2 coming from an unwinder 3 and unloads them into a feed path P that passes through a tail sealer 8. The tail or outer edge of the wound web material in each log R is sealed to the outer surface of the log by the tail sealer 8. Arranged downstream of the tail sealer 8 is a measuring station, located in which is a measuring device 9 that measures one or more parameters of logs R picked up randomly from the feed path P of the logs along the converting line 1. Arranged downstream of the measuring station, there can be one or more further stations of the converting line, for example a storage unit 11 and a log saw 12 that cuts each log into rolls of smaller axial dimensions, which are then packaged in a packaging section (not shown) of the converting line 1.

The measuring device 9 and its operating cycle will be described in detail hereunder, with specific reference to FIGS. 2 to 9. The letter P indicates the feed path of the logs R, which in the device 9 is defined by a chute 21 or other surface for supporting the logs. In the illustrated embodiment, the feed path P is configured so as to allow feed by gravity; the logs R roll on the chute 21, which is inclined to facilitate feed of the logs R. Nonetheless, it would also be possible to provide a feed path in which the logs R are controlled and moved by feed members.

The measuring device 9 comprises a stationary bearing structure, which has a cross member 25 extending transverse to the feed path P, and hence transverse to the direction of feed of the logs R along the feed path P, represented by the arrow P.

One or more pick-up members 27 are mounted on the cross member 25. In the illustrated embodiment two pick-up members 27 are provided.

In the illustrated embodiment, the pick-up members 27 are substantially the same as one another. In other embodiments, the pick-up members 27 can be symmetrical with respect to a vertical plane, parallel to the feed path P of the logs R.

The pick-up members 27 are spaced from one another along the cross member 25, so as to engage the logs R, on which the measurements are carried out. In the illustrated embodiment, the pick-up members 27 are located in two positions fixed with respect to the transverse direction (orthogonal to P), but it would also be possible to mount the pick-up members 27 so that their mutual distance and/or their position with respect to the direction transverse to the feed path P is adjustable, for example as a function of the axial length of the logs R.

The measuring device 9 further comprises two blocking heads 29, substantially symmetrical to each other with respect to a plane orthogonal to the cross member 25 and located on opposite sides of the feed path P. The two blocking heads 29 are located externally to the pick-up members 27 and are movable according to the double arrows f29 parallel to the cross member 25 to move toward and away from each other.

The structure and the function of the pick-up members 27 is described in detail below with reference in particular to FIGS. 2, 3, 4, 6 and 7.

Figure 2:
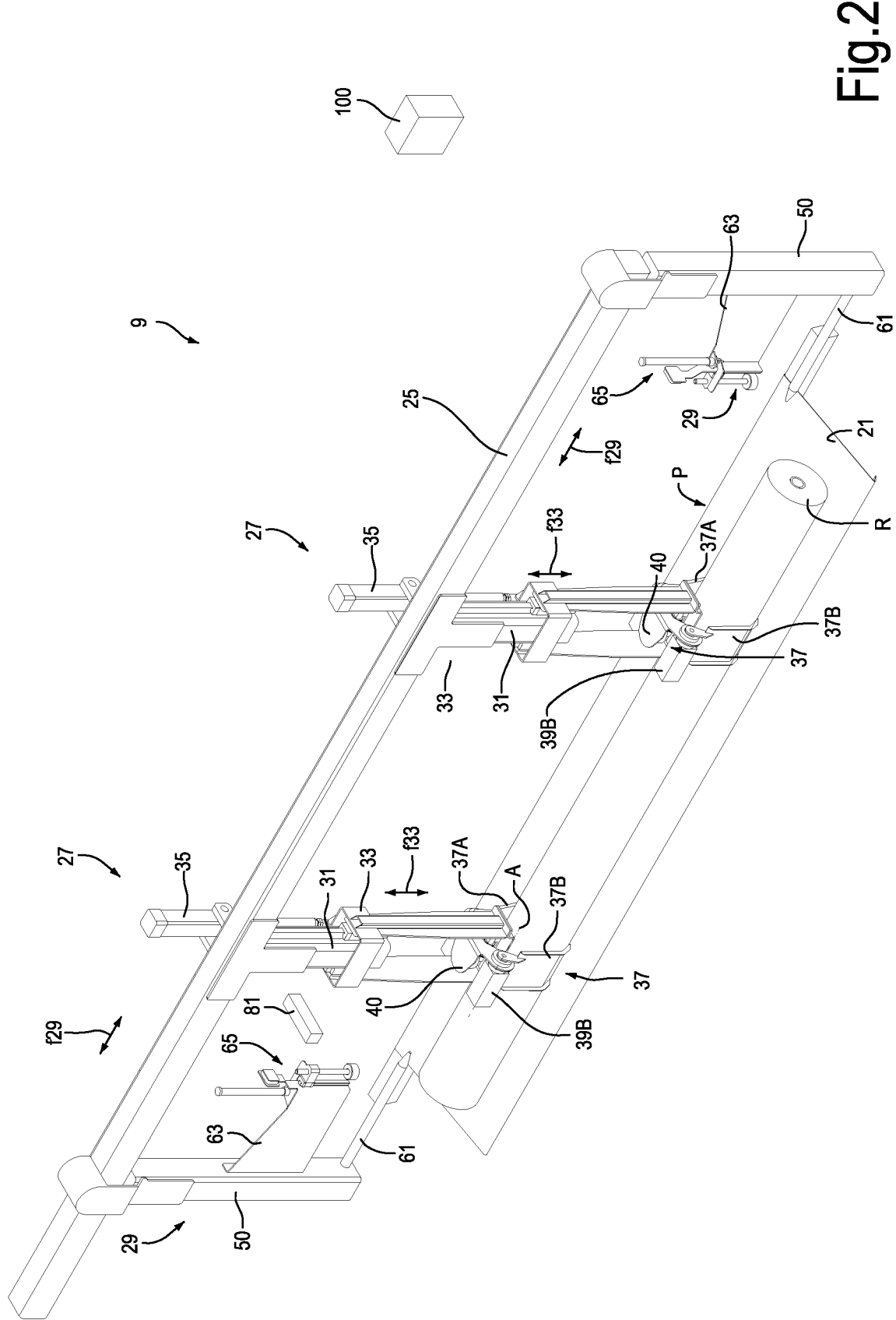
FIG. 2 shows an axonometric view of the measuring device.
Figure 3:
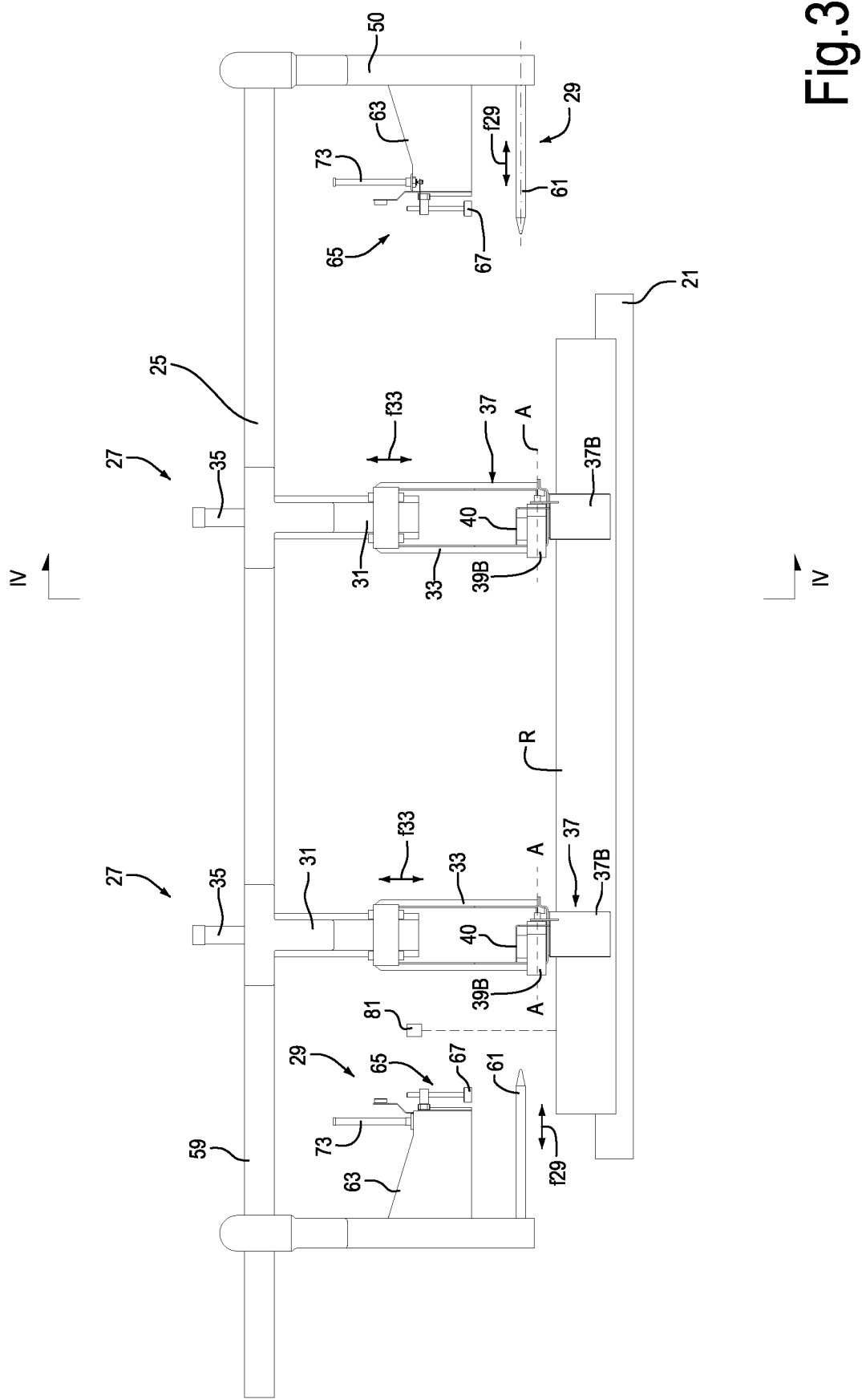
FIG. 3 shows a front view of the device of FIG. 2.
Figure 4:
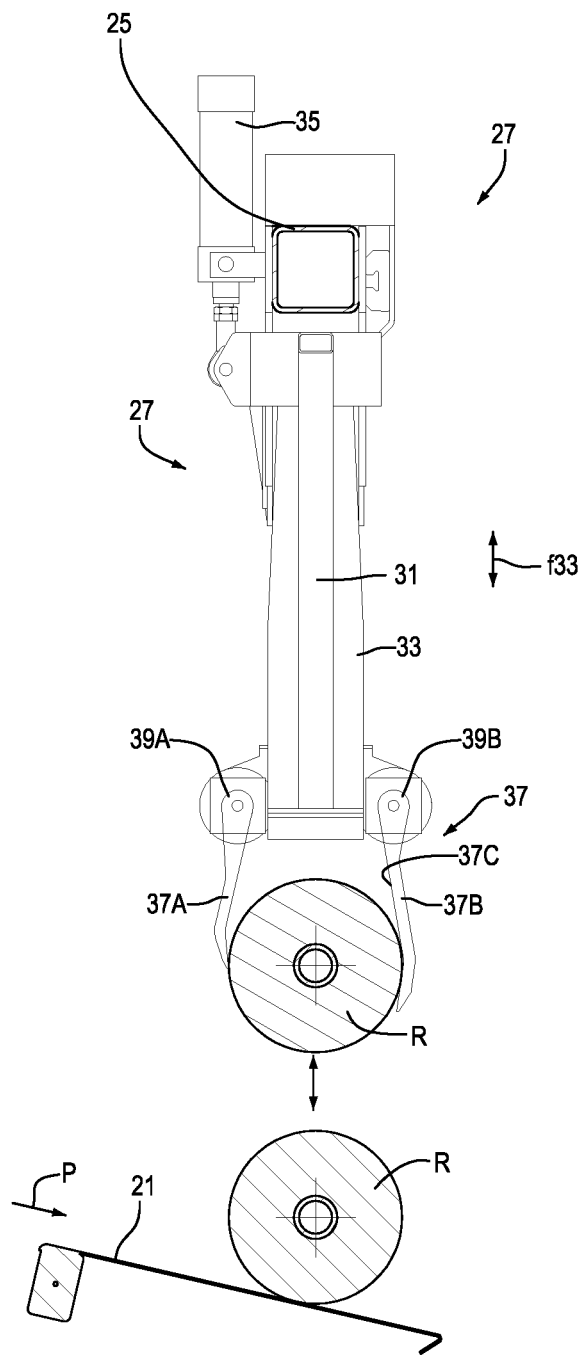
FIG. 4 shows a section according to IV-IV of FIG. 3.

Each pick-up member 27 is movable along a respective vertical upright 31, integral with the cross member 25. A load-bearing structure comprising a slide 33 of the pick-up member 27 slides along the upright 31 according to the double arrow f33. In FIGS. 2 and 3 the two pick-up members 27 are shown in their lowest position.

The lifting and lowering movement according to f33 of the slides 33 is controlled by respective linear actuators 35, for example piston-cylinder actuators.

A gripper 37, comprising a first jaw 37A and a second jaw 37B, is constrained to each slide 33. The two jaws 37A, 37B are different from each other. More precisely, the first jaw 37A, which is located upstream of the second jaw 37B with respect to the direction of feed of the logs R along the feed path P, is shorter than the second jaw 37B. In the illustrated embodiment, the second jaw 37B comprises, by way of example, a concave surface 37C against which the log R is pushed by the first jaw 37A, as will be described in greater detail below with reference to an operating cycle.

Each of the two jaws 37A, 37B is controlled by its own actuator. A first actuator 39A controls the first jaw 37A and a second actuator 39B controls the second jaw 37B. The actuators 39A, 39B can be electronically controlled electric motors or other rotary actuators, which move the two jaws 37A, 37B about rotation axes A parallel to each other and parallel to the cross member 25. The use of two separate actuators 39A, 39B for the two jaws 37A, 37B of each gripper 37 allows the two jaws 37A, 37B to carry out rotation movements about the axes A that are staggered from each other, for reasons that will be apparent from the description of an operating cycle. Therefore, the actuators are independent but controlled so as to carry out coordinated movements with respect to each other.

The jaws 37A. 37B and the actuators 39A, 39B are supported by the slide 33 by means of a support 40, which is constrained to the slide 33 with the interposition of a load cell 41. In this way, the load cell 41 of each gripper 37 can measure the weight of a log R engaged by the grippers 37 in the manner described hereunder.

Each blocking head 29 has a structure described below with reference in particular to FIGS. 2, 3 and 5. Each blocking head 29 comprises an upright 50 engaged with guides integral with the cross member 25, not shown, to move according to the double arrow f29 parallel to the cross member 25. The movement according to f29 is imparted to each measuring head 29 by an actuator, not shown, for example an electronically controlled electric motor.

Figure 5:
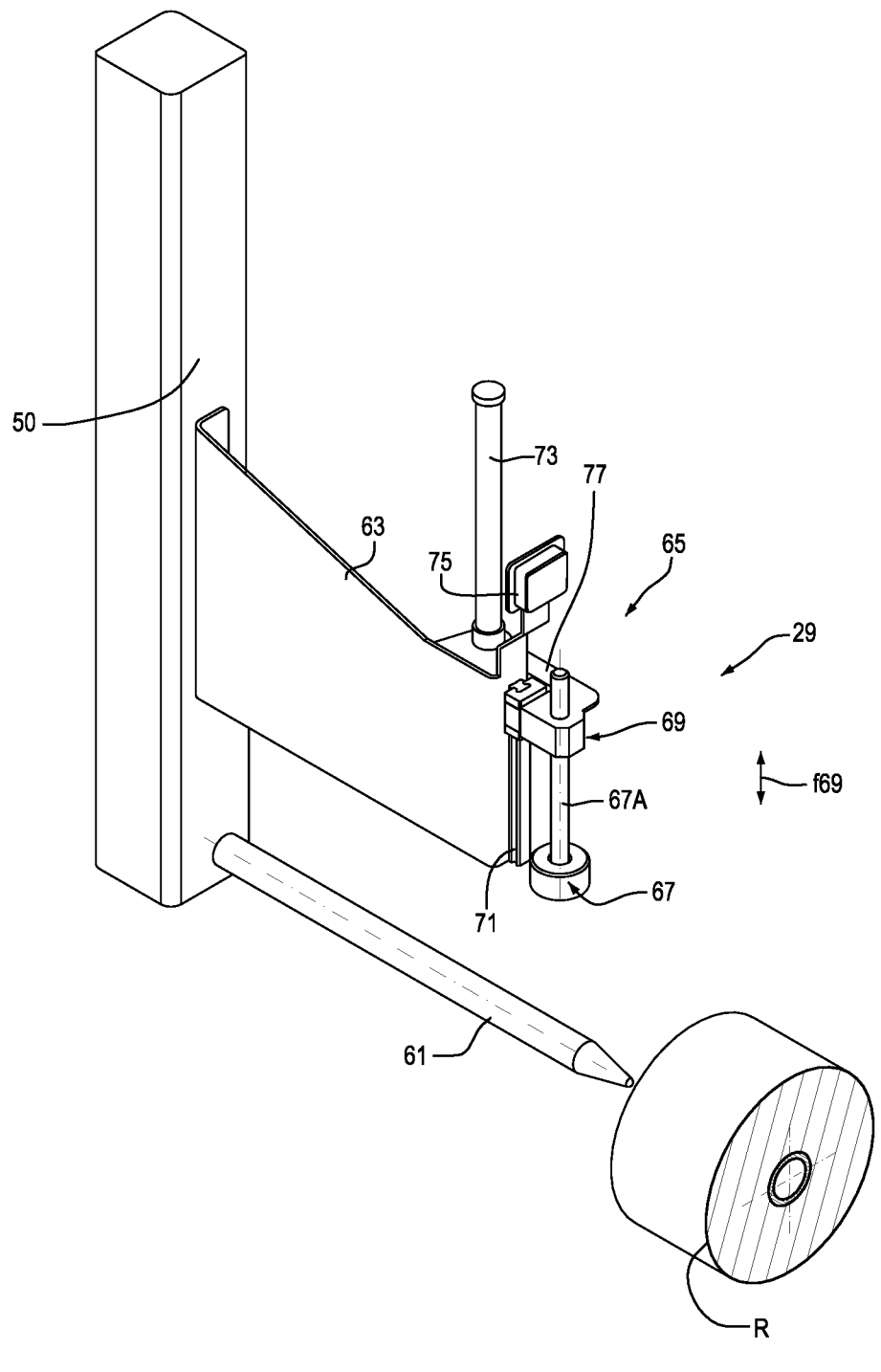
FIG. 5 shows an axonometric view of one of the two blocking heads.
Figure 6:
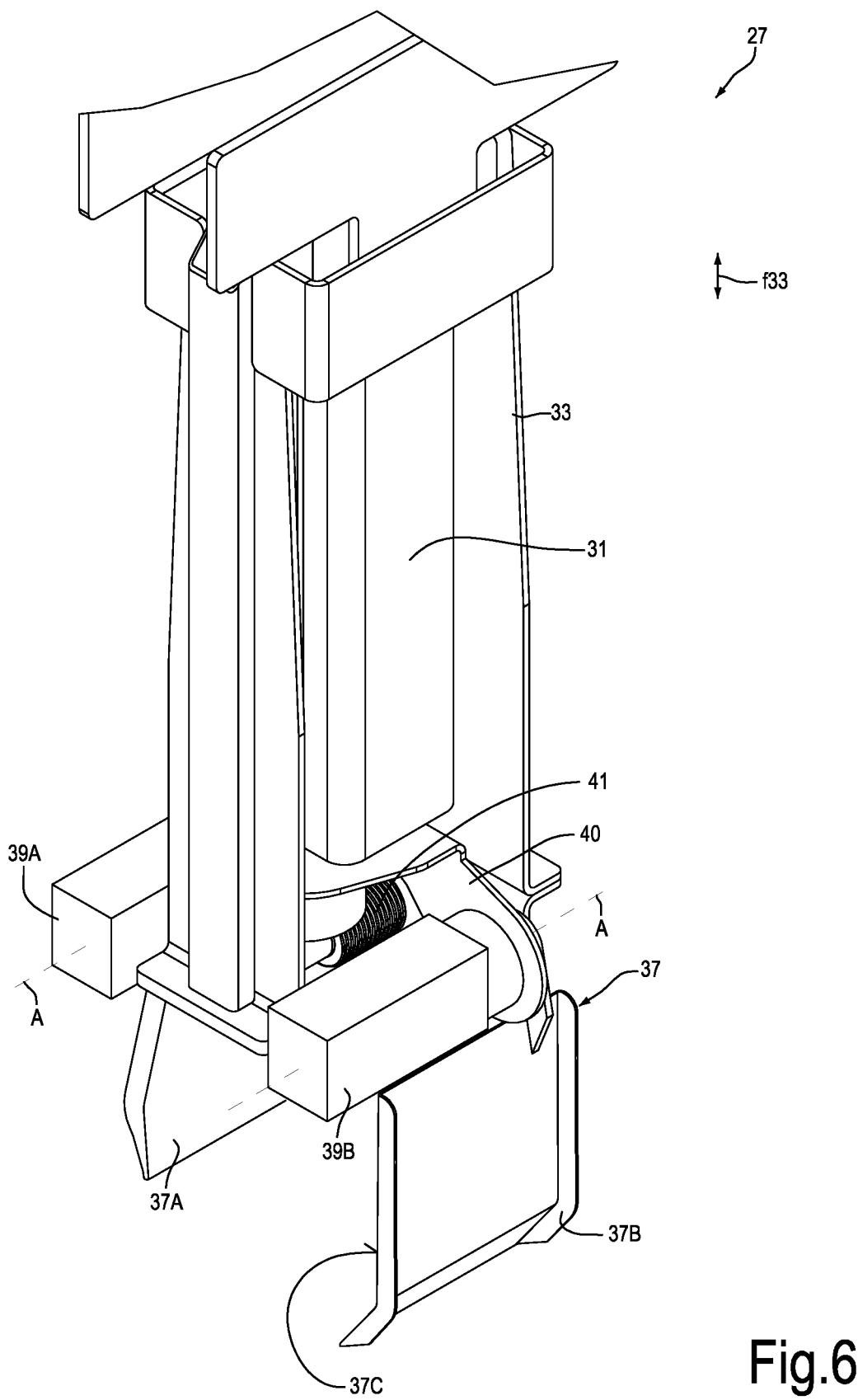
FIG. 6 shows an axonometric view of one of the pick-up members of the logs.
Figure 7:
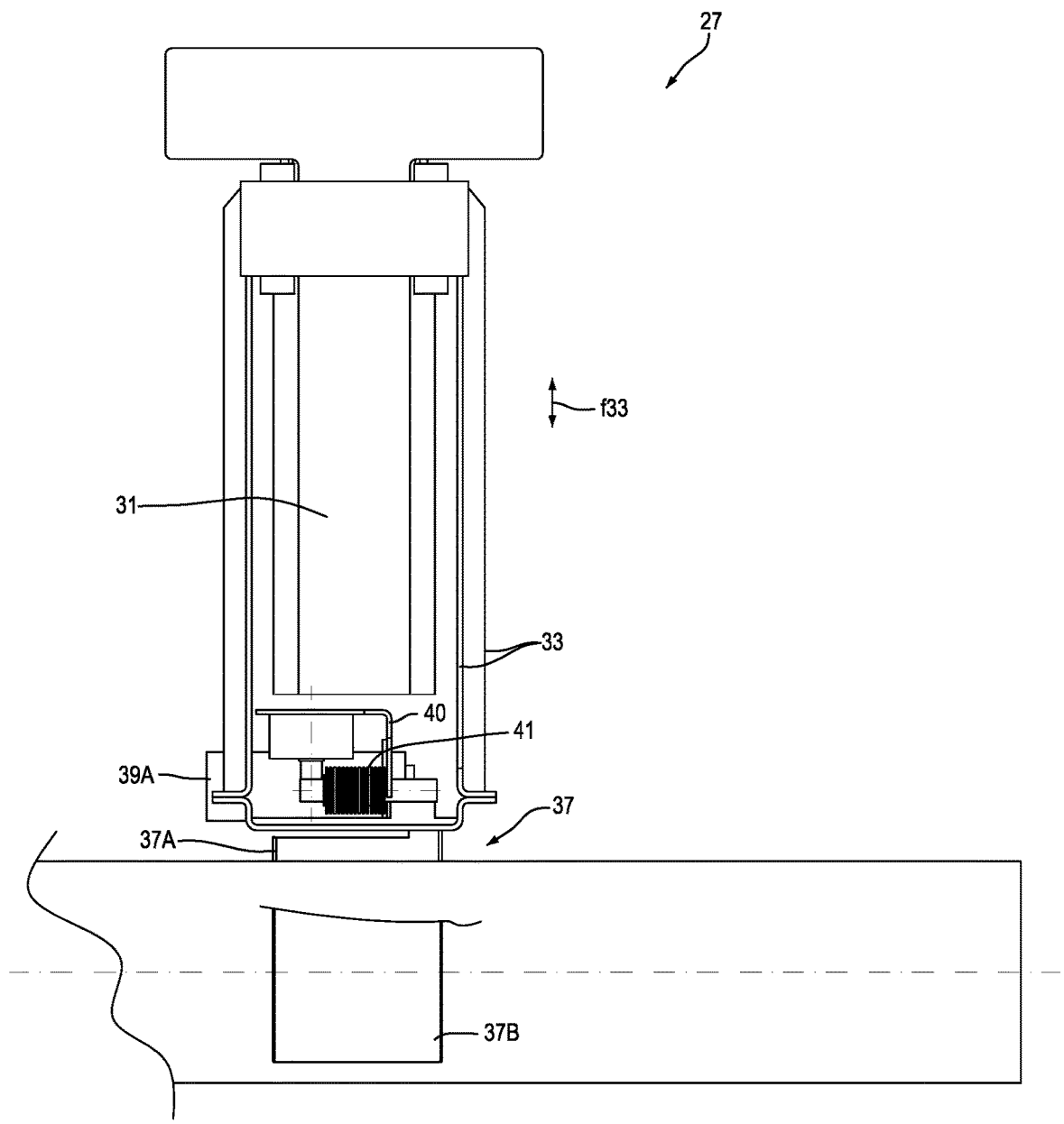
FIG. 7 shows a front and partially sectional view on a vertical plane of the pick-up member of FIG. 6.

With reference in particular to FIG. 5, a tailstock 61, oriented parallel to the cross member 25, is fixed in the lower part of the upright 50 of each blocking head 29. The two tailstocks 61 of the two blocking heads 29 are oriented facing each other and are coaxial.

An arm 63, which carries log firmness measuring members, indicated as a whole with 65, can be fixed on the upright 50 of the blocking head 29, above the respective tailstock 61. The firmness measuring members 65 comprise a presser 67 integral with a rod 67A integral with a slide 69, which slides in vertical direction according to the double arrow f69 along a guide 71 integral with the arm 63. In other embodiments, the measuring member 65 can be provided on only one of the two blocking heads 29.

A linear actuator 73, for example a piston-cylinder actuator, is connected to the slide 69 and controls the movement thereof according to the double arrow f69. A bracket 77 constrains the rod of the linear actuator 73 to the slide 69. A measuring arrangement, i.e., a sensor 75, for example a laser sensor, measures the position of the slide 69 and hence of the presser 67 with respect to the arm 63 and with respect to the tailstock 61.

The presser 67 is calibrated in diameter and weight and applies a known compression force on the log R that is positioned in the measuring device. By means of the laser sensor 75, or other suitable sensor, the degree of penetration of the presser 67 into the wound web material of the log R is determined in order to detect the firmness, as described in greater detail below.

In addition to the members described herein, a measuring system of the diameter of the logs R is also associated with the measuring device 9. Purely by way of example, in FIG. 2 this measuring system is represented as a laser emitter 81, which detects the passage of the logs and determines the diameter thereof. In some embodiments, the measuring system 81 is positioned so as to measure the diameter of a log R when this is close to the grippers 37 of the pick-up members 27.

In brief, the measuring cycle is as follows. Measurements are carried out randomly only on some logs R being fed along the feed path P through the measuring device 9. The logs can be chosen randomly, either by an operator, or in a programmed manner, for example one log every N logs produced, or in any other suitable way. Operation of the measuring device 9 is controlled by means of a control unit indicated schematically with 100 in FIG. 2 and that can be interfaced with a higher-level control unit, which manages the converting line 1. The control unit 100 can advantageously be interfaced with the sensors and the actuators described above, in particular with the actuators 39A 39B, 35, 73 and with the sensors 41, 75, 81.

Figure 8A:
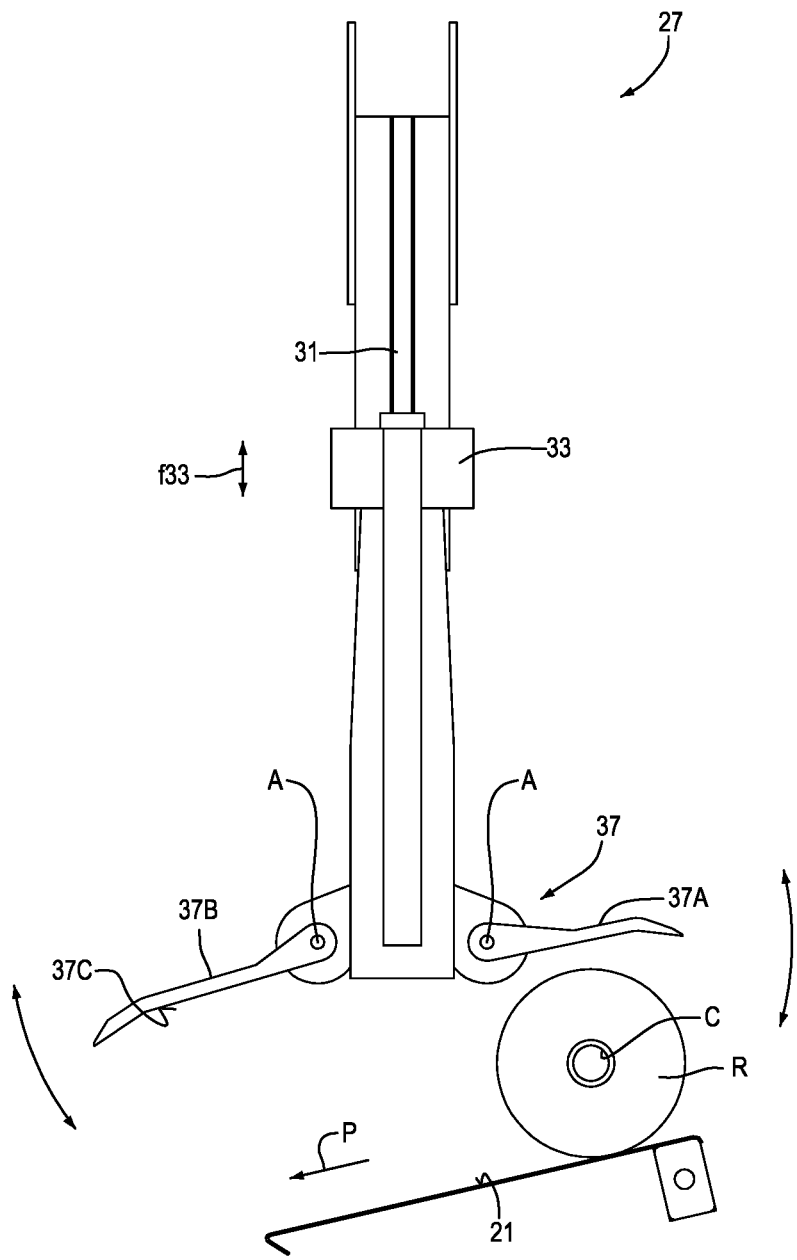

The sequence of FIGS. 8A-8J illustrates in detail the operation of a pick-up member 27. In FIG. 8A the pick-up member 27 is in an idle position and is above the feed path P of the logs R, which can pass through the measuring device 9 without interacting therewith.

Figure 8B:
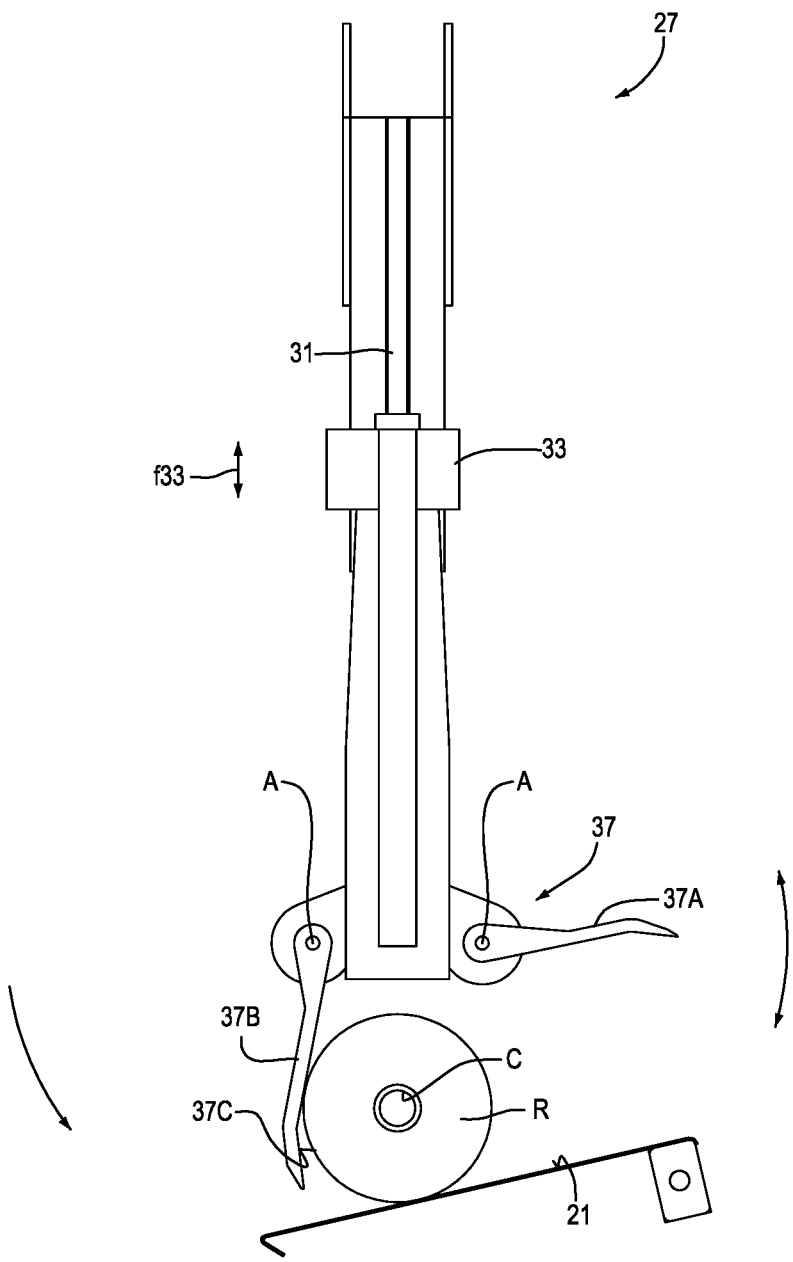
Figure 8C:
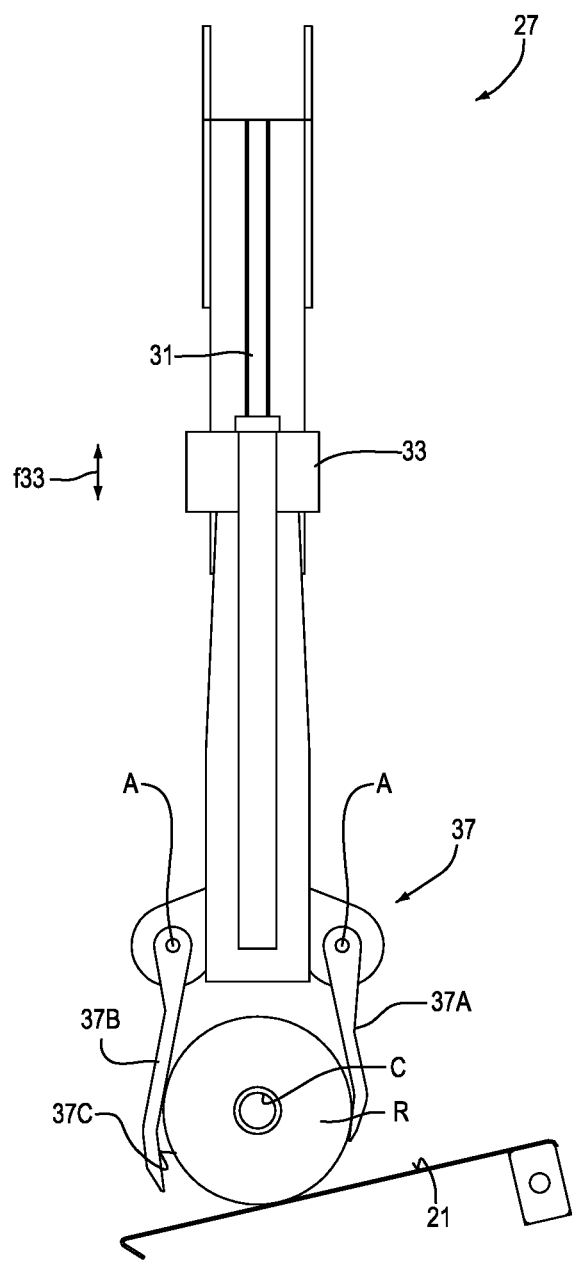
Figure 8E:
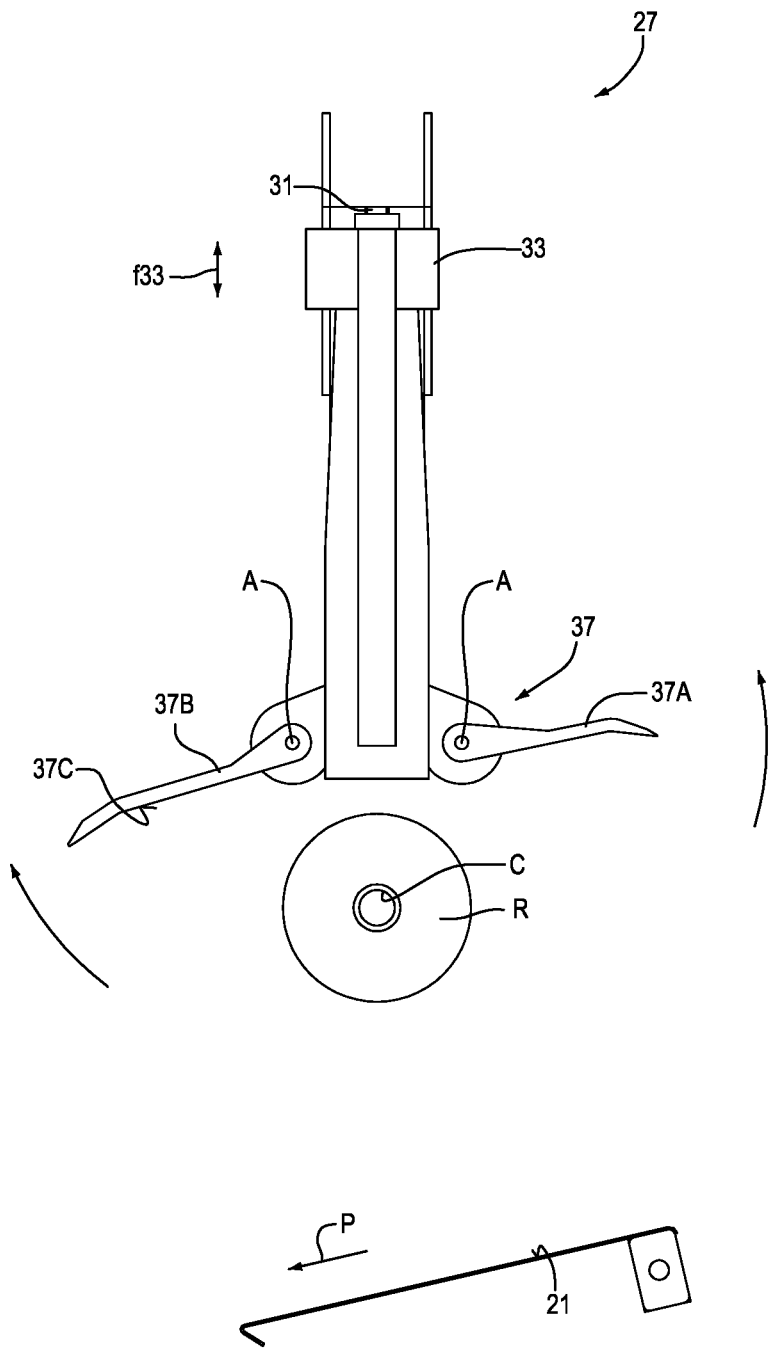
Figure 8F:
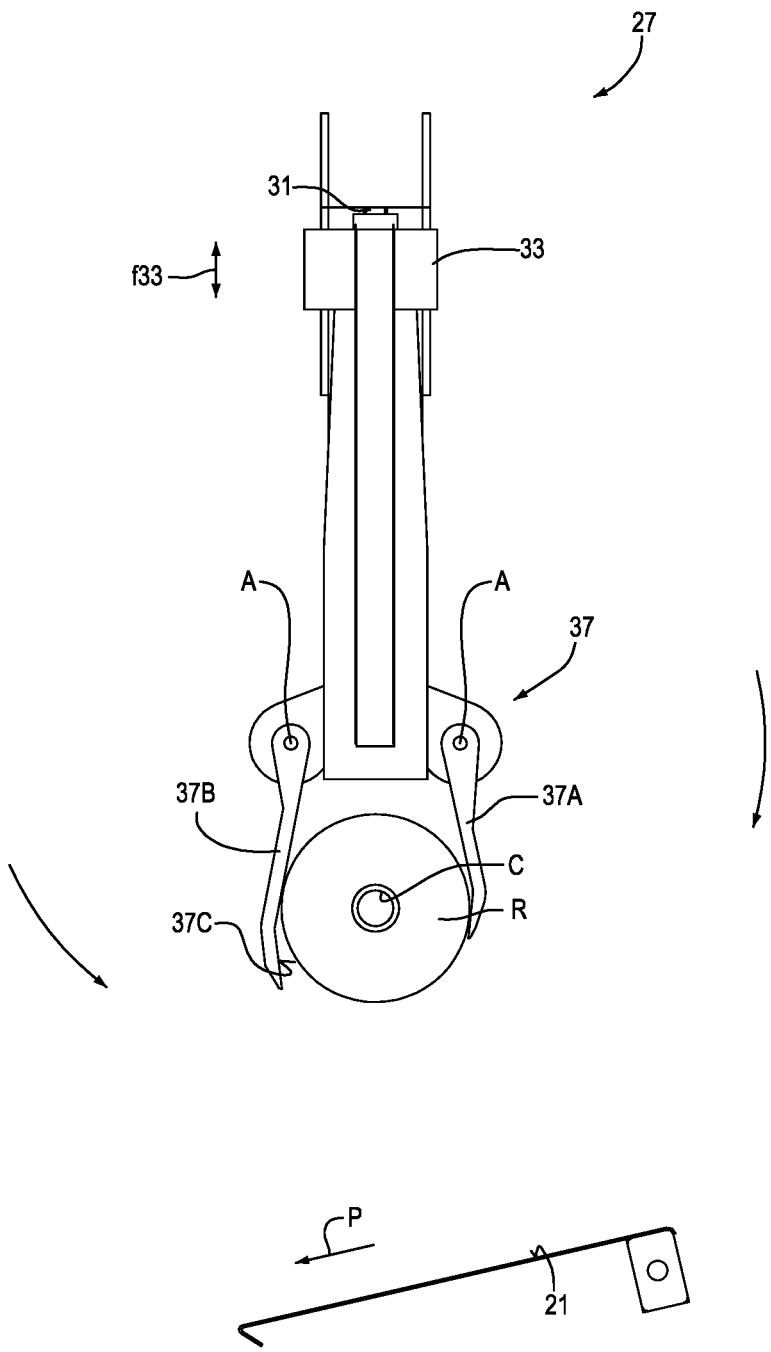
Figure 8G:
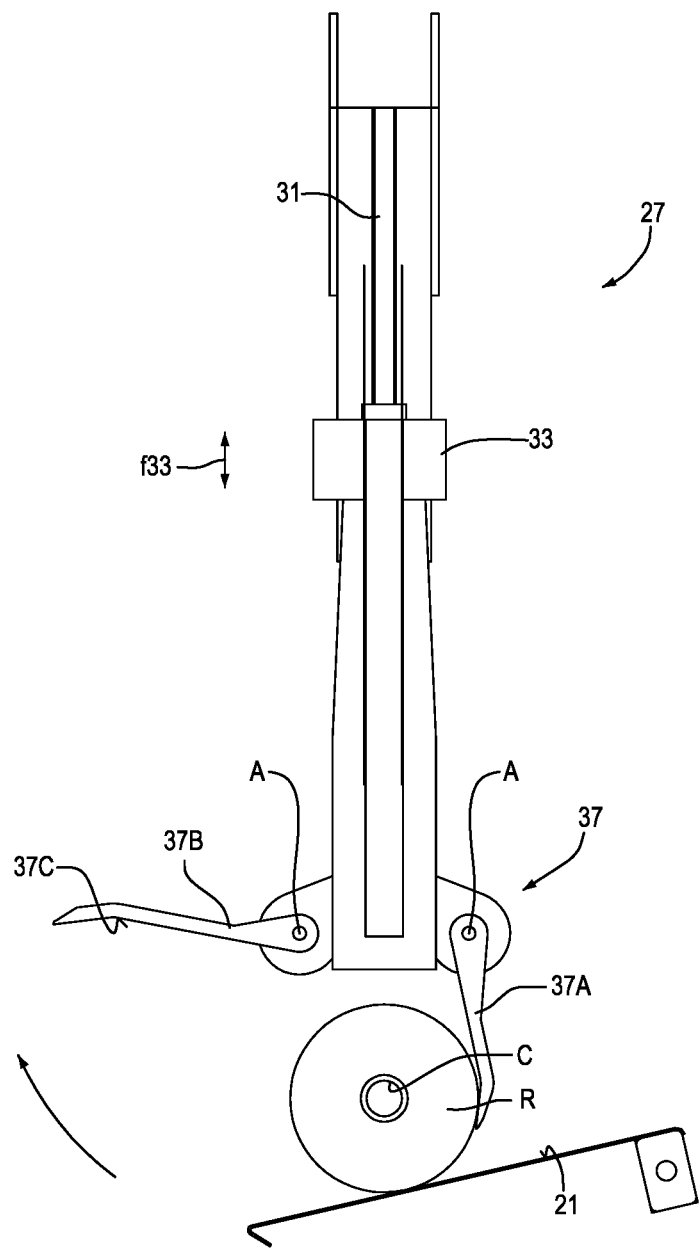
Figure 8I:
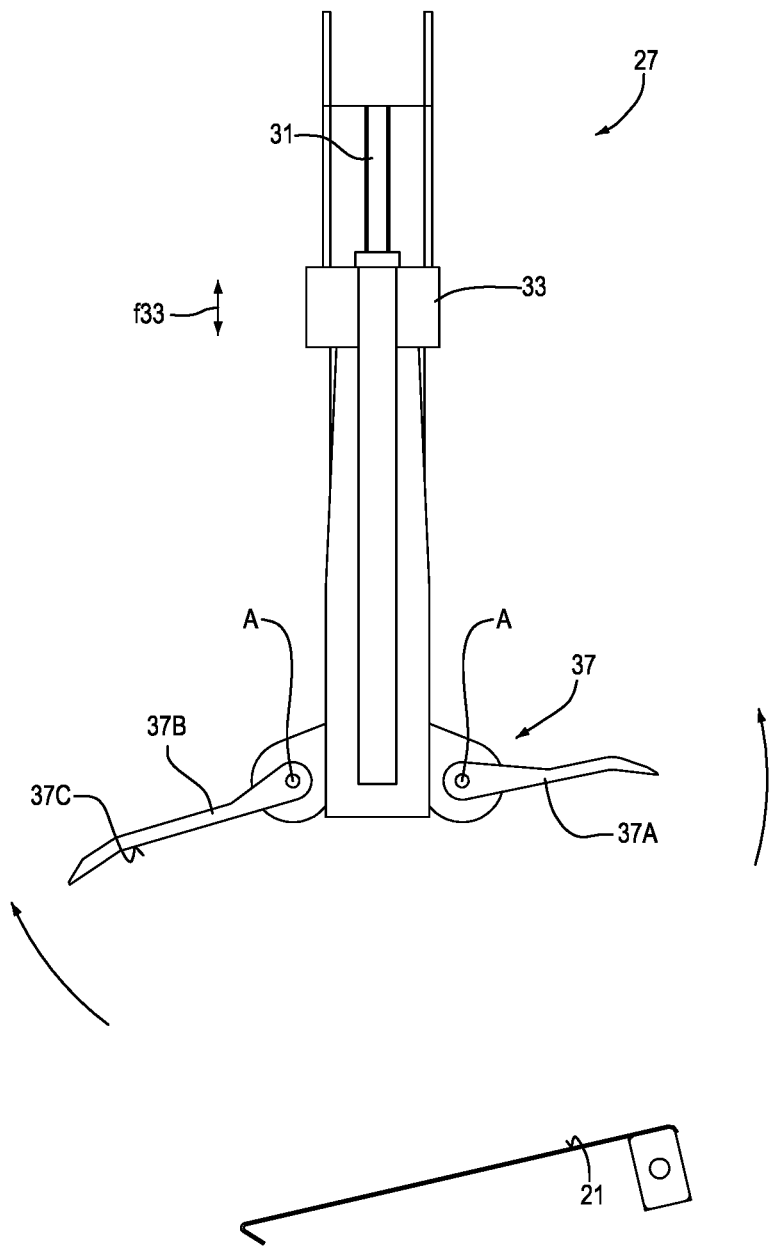
Figure 8J:
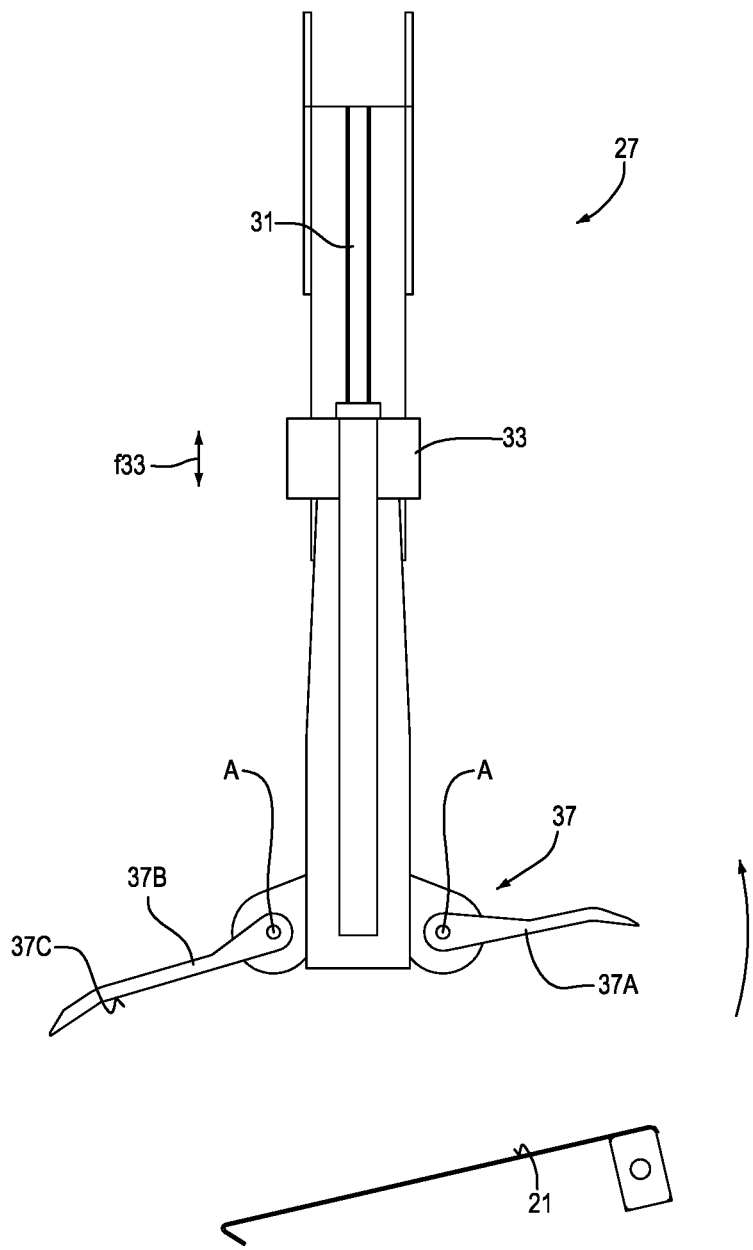

FIGS. 8B-8J show the pick-up sequence of a single log R from the feed path P, the transfer thereof to the blocking heads 29 and the release thereof into the feed path P (FIG. 8G), substantially in the same position from which it was picked up (FIG. 8B).

To pick up a log R, the pick-up members 27 are lowered toward the chute 21 to a height such as to interact with the logs R. The second jaw 37B of the gripper 37 is rotated downward (FIG. 8B), in order to stop the approaching log R. Once the approaching log R is in contact with the second jaw 37B, condition that can be detected, for example, by a photocell, not shown, the first jaw 37A of the gripper 37 is lowered, closing the gripper 37 and engaging the log R in the gripper.

After the log R has been gripped, the pick-up members 27 are lifted (FIG. 8D) to take the log R out of the feed path of the logs P. More in particular, the log R is taken with its tubular winding core C in alignment with the tailstocks 61 of the blocking assembly 29, so that these, by moving toward each other (arrow f29), are inserted from opposite ends in the tubular winding core C. When the tailstocks 61 have engaged the log R, the grippers 37 open (FIG. 8E) and release the log R on the tailstocks, so that the firmness of the log is measured, in the manner described below with reference to the sequence of FIGS. 9A-9E. After the firmness measurement has taken place, the grippers 37 close again (FIG. 8F), the tailstocks 61 are extracted from the tubular core C and the grippers 37 are lowered to release the log R on the chute 21 in the feed path P. The log R continues rolling along the path, while the pick-up members 27 are lifted again (FIG. 8H) and the jaws 37A, 37B open (FIG. 8I) and finally the pick-up members 27 with the open grippers move toward the chute 21 (FIG. 8J) in the position in which a new log R can be picked up, repeating the above described sequence.

In practice, the logs R are picked up randomly, with a frequency that can be fixed or variable, automatically and/or manually controlled, so as to repeat with the most suitable frequency a random control on the parameters (diameter, weight and compactness) of the logs produced by the rewinder.

During the steps described above, and preferably before the step of FIG. 8E, the weight of the log R is measured by means of the load cells.

The sequence of FIGS. 9A-9H illustrates the operations carried out during the measuring cycle by the blocking heads 29 and by the measuring assembly 65. The operations illustrated in the sequence of FIGS. 9A-9H are coordinated with the operations carried out by the pick-up members 27 illustrated in FIGS. 8A-8J.

In FIG. 9A the pick-up members 27 have carried the log R in alignment with the tailstocks 61. By means of a laser sensor or other suitable means, such as a video camera, the position of the log R for correct insertion of the tailstocks 61 is detected. Centering between the tubular core C of the log R and the tailstocks 61 can take place with a lifting and lowering movement of the grippers 37 and with a synchronized rotation movement of the jaws 37A, 37B of each gripper 37 that causes a movement with a horizontal component of the log R. For embodiments with two or more grippers 37, these can be controlled separately from one another, so as to be able to center the two ends of the tubular winding core C relative to the two tailstocks 61.

Figure 9B:
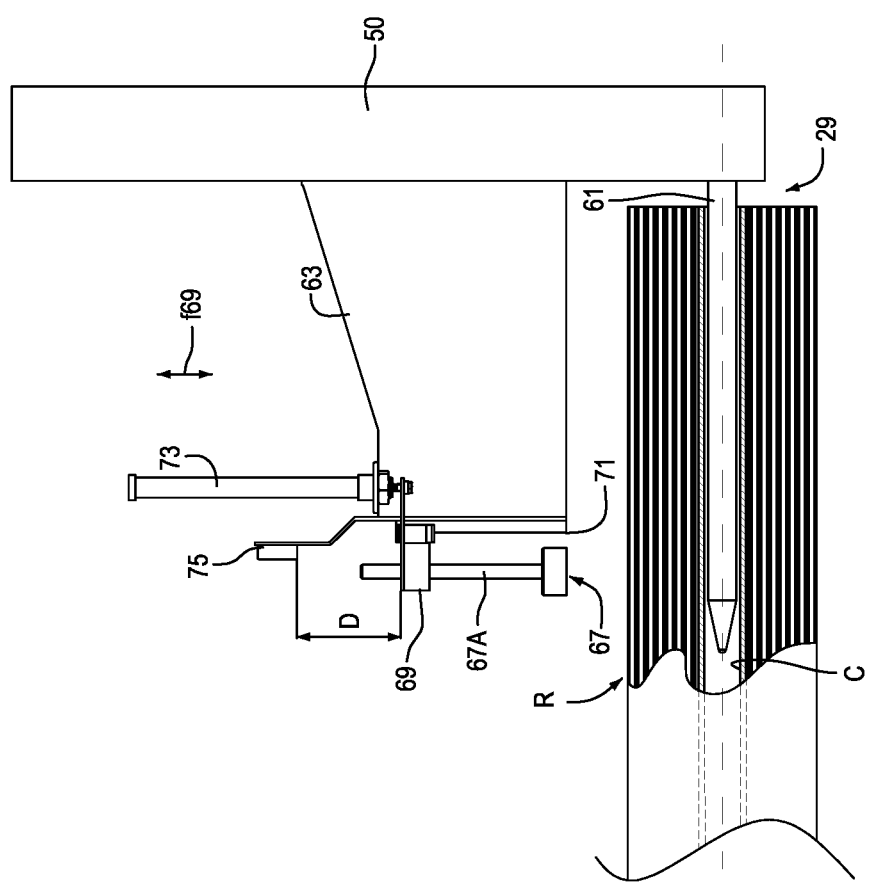
Figure 9C:
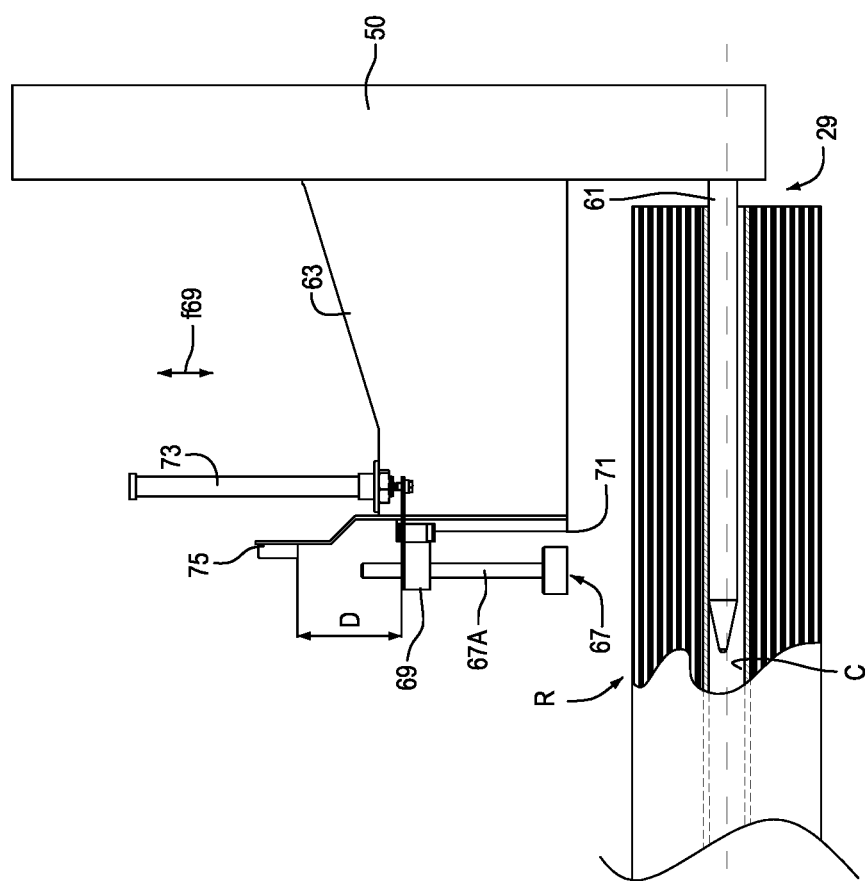

Once the tailstocks 61 and the tubular winding core C have been aligned, the two blocking heads 29 can be moved toward each other so as to insert the tailstocks 61 in the tubular core C, see FIG. 9B. In this step, the log R is still engaged by the jaws 37A, 37B of the grippers 37.

Figure 9E:
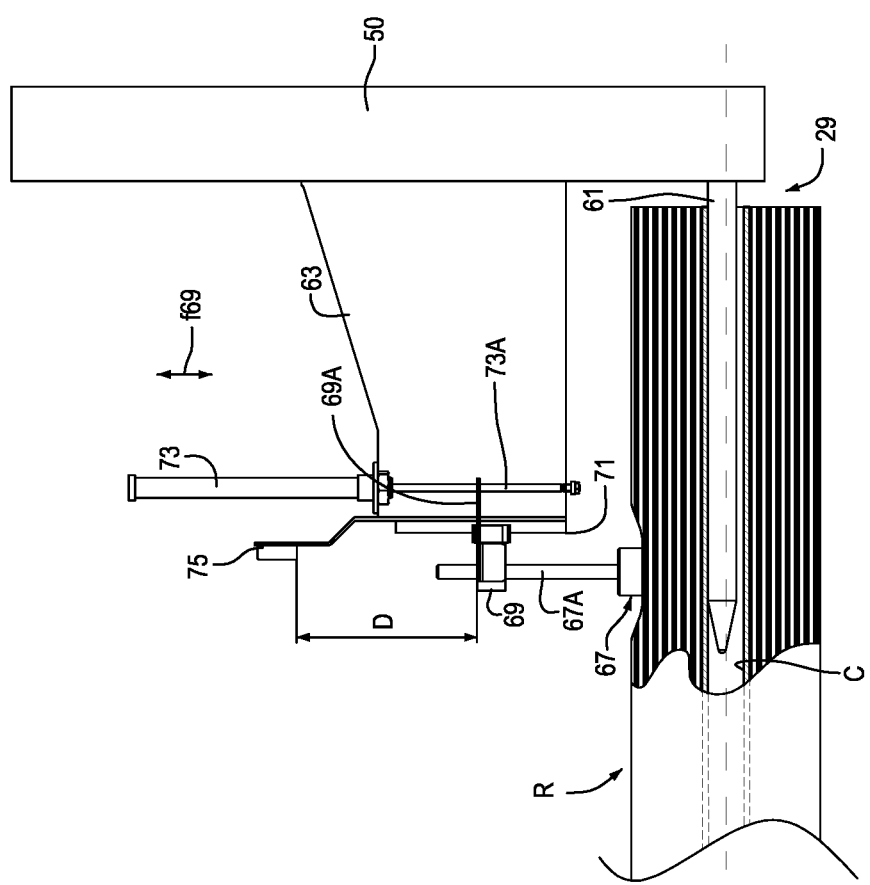

In the subsequent step (FIG. 9C), the jaws 37A, 37B of the grippers 37 open and the log R is placed on the tailstocks 61, which come into contact with the inner surface of the tubular core C. In this position the log firmness can be measured. To this end, the linear actuator 73 lowers the presser 67. The actuator 73 comprises a rod 73A that engages in a hole of a plate 69A of the slide 69 (FIG. 9D), so that the actuator 73 can extend completely, while the presser 67 comes into contact with the outer surface of the log R and stops at a height that is determined by the extent to which the wound web material in the log R is compressed under the weight of the presser 67 alone. FIG. 9E schematically shows how the presser 67 penetrates the theoretical cylindrical surface of the log R compressing the turns of wound web material. The penetration depth is proportional to softness, and hence is a function of the firmness of the log R.

The sensor 75 detects the position of the log R with respect to the position of the presser 67. When the presser 67 reaches the surface of the log (FIG. 9D) the sensor detects the degree of penetration P1 of the presser 67 based on the diameter of the log R, which was measured or will be measured by the sensor 81.

The compression measured is determined solely from the variation of thickness of the material comprised between the presser 67 and the tailstock 61. Therefore, the firmness measurement obtained is not affected by errors, typical of prior art measuring systems, due to compression of the tubular winding core during measurement.

The random measurement of the firmness of the log R can be used to take action on the production parameters of the converting line. Typically, the firmness of the log can be corrected, if the measurement is outside an admissible range, by acting on the tension of the web material in the rewinder and/or by acting on the embossing conditions of the plies forming the web material of the log, in a manner known per se by those skilled in the art.

What is claimed is:

1. A device for measuring parameters of a log of wound web material, comprising:
    a feed path of the logs, configured to feed the logs in a direction orthogonal to the axis of the logs;
    at least one pick-up member adapted to:
        pick up individual logs from a pick-up position along the feed path and move the individual logs to a measuring position; and
        transfer each log from the measuring position back to the feed path.

2. The device of claim 1, comprising two pick-up members spaced from one another in a direction transverse to the feed path of the logs.

3. The device of claim 1, wherein said at least one pick-up member is adapted to measure at least one parameter of the picked-up log, while the log is engaged with the at least one pick-up member.

4. The device of claim 1, wherein said at least one pick-up member is adapted to transfer each log picked up from the measuring position back to the pick-up position along the feed path of the logs, the at least one pick-up member comprising a lifting and lowering actuator, adapted to transfer the at least one pick-up member from the pick-up position to the measuring position and vice versa.

5. The device of claim 1, wherein the at least one pick-up member comprises a log weight measuring member.

6. The device of claim 1, wherein the at least one pick-up member comprises a gripper with a first jaw and a second jaw, the first jaw being located upstream of the second jaw with respect to the direction of feed of the logs along the feed path; and wherein the first jaw and the second jaw pivot about respective pivot axes orthogonal to the direction of feed of the logs along the feed path and parallel to the axes of the logs in the feed path.

7. The device of claim 6, wherein each gripper comprises a first actuator for controlling the movement of the first jaw and a second actuator for controlling the movement of the second jaw.

8. The device of claim 6, wherein the second jaw is longer than the first jaw.

9. The device of claim 5, wherein the at least one pick-up member comprises a gripper with a first jaw and a second jaw, the first jaw being located upstream of the second jaw with respect to the direction of feed of the logs along the feed path; wherein the first jaw and the second jaw pivot about respective pivot axes orthogonal to the direction of feed of the logs along the feed path and parallel to the axes of the logs in the feed path; and wherein each log weight measuring member comprises a load cell, and wherein the load cell is located between a support, on which the respective gripper is mounted, and a bearing structure, movable relative to the feed path of the logs to transfer the gripper from the pick-up position to the measuring position, and vice versa.

10. The device of claim 1, comprising a pair of blocking heads, located above the feed path and at the sides of the feed path; wherein at least one of the blocking heads comprises a log firmness measuring member; wherein the blocking heads are aligned transverse to the feed path along a direction orthogonal to the direction of feed of the logs along the feed path and parallel to the direction of the axes of the logs in the feed path; and
wherein the at least one pick-up member is adapted to position each picked-up log in a measuring position, in which the log interacts with the blocking heads.

11. The device of claim 10, wherein each blocking head comprises a respective log firmness measuring member.

12. The device of claim 10, wherein each log firmness measuring member comprises a presser adapted to apply a predetermined load against the surface of a log picked up from the feed path and a measuring arrangement of the degree of penetration of the presser into the log as a result of the predetermined load applied by the presser.

13. The device of claim 10, wherein: each blocking head is movable in a direction orthogonal to the direction of feed of the logs along the feed path and parallel to the axes of the logs; and wherein each blocking head comprises a tailstock adapted to be inserted into a tubular winding core of the logs; the tailstocks of the two blocking heads are aligned with and symmetrical to each other; and the movement of the blocking heads is controlled so as to insert the two tail-stocks in opposite ends of the winding core of a log in the measuring position and extract them from said ends.

14. The device of claim 10, wherein each blocking head is movable in a direction orthogonal to the direction of feed of the logs along the feed path and parallel to the axes of the logs; wherein each blocking head comprises a tailstock adapted to be inserted into a tubular winding core of the logs; the tailstocks of the two blocking heads are aligned with and symmetrical to each other; wherein the movement of the blocking heads is controlled so as to insert the two tailstocks in opposite ends of the winding core of a log in the measuring position and extract them from said ends; and wherein the presser is adapted to coact with the respective tailstock to apply a force orthogonal to the tailstock and cause compression of the material of the log comprised between the presser and the tailstock.

15. The device of claim 13, wherein each blocking head comprises a centering system between the tailstock and the winding core of the log picked up from the feed path.

16. The device of claim 15, wherein the centering system is interfaced with a control unit that, based on signals of the centering system, moves the at least one pick-up member relative to the tailstocks.

17. The device of claim1, comprising a log diameter measuring system.

18. A method for manufacturing logs of web material, comprising the following steps:
sequentially producing logs of web material;
feeding the logs of web material in a feed path, in which the logs of web material are fed in a direction orthogonal to the axis of the logs;
by at least one pick-up member, picking up a log from a pick-up position along the feed path of the logs;
measuring at least one parameter of the log picked up;
returning, by said at least one pick-up member, the log to the feed path.

19. The method of claim 18, wherein the step of picking up the log is carried out by two pick-up members spaced from each other in a direction transverse to the feed path of the logs.

20. The method of claim 18, wherein the step of measuring at least one parameter of the picked-up log is carried out while the log is engaged with the at least one pick-up member.

21. The method of claim 20, wherein the step of measuring at least one parameter of the picked-up log when the log is engaged with the at least one pick-up member comprises the step of measuring the weight of the log by means of sensors positioned on the at least one pick-up member.

22. The method of claim 18, wherein the at least one pick-up member returns the log to the pick-up position along the feed path.

23. The method of claim 18, further comprising the following steps:
by the at least one pick-up member, transferring the log picked up from the feed path to a measuring position, in which opposite ends of the log interact with a pair of blocking heads, arranged above the feed path and at the sides thereof; wherein the blocking heads are aligned in a direction transverse to the direction of feed and parallel to the axis of the logs along the feed path;
measuring the log firmness by a measuring system installed on one of the blocking heads or by two measuring systems, each installed on a respective one of the blocking heads.

24. The method of claim 18, further comprising the following steps:
in the measuring position, inserting into each end of a tubular winding core of the log, a respective tailstock of the respective blocking head and releasing the log from the at least one pick-up member;
by means of a presser, applying a force on the outer surface of the log, approximately orthogonally to at least one of said tailstocks while the log is supported by the tailstocks;
measuring the degree of compression of the material of which the log is formed between the presser and the tailstock.

25. The method of claim 18, further comprising the step of measuring the diameter of the log.

26. The method of claim 18, further comprising the step of modifying at least one log production parameter as a function of a parameter of the log selected from the group consisting of: a log weight, a log diameter, a log firmness; a combination thereof.

27. The method of claim 18, further comprising the step of measuring the diameter of the log before the log is picked up by the at least one pick-up member.

* * * * *